United States Patent
Gatto et al.

(10) Patent No.: US 9,486,367 B2
(45) Date of Patent: Nov. 8, 2016

(54) ABSORBENT ARTICLE WITH LOTION COMPRISING A POLYPROPYLENE GLYCOL MATERIAL

(75) Inventors: Joseph Anthony Gatto, Loveland, OH (US); Brent Taylor Ginn, Monroe, OH (US); Robert Ya-lin Pan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 744 days.

(21) Appl. No.: 12/032,099

(22) Filed: Feb. 15, 2008

(65) Prior Publication Data

US 2008/0200894 A1 Aug. 21, 2008

Related U.S. Application Data

(60) Provisional application No. 60/901,793, filed on Feb. 16, 2007.

(51) Int. Cl.
| | |
|---|---|
| *A61F 13/15* | (2006.01) |
| *A61F 13/511* | (2006.01) |
| *A61L 15/26* | (2006.01) |
| *A61L 15/34* | (2006.01) |
| *A61F 13/84* | (2006.01) |
| *A61L 15/48* | (2006.01) |
| *A61L 15/50* | (2006.01) |
| *A61F 13/51* | (2006.01) |

(52) U.S. Cl.
CPC .......... *A61F 13/15* (2013.01); *A61F 13/51113* (2013.01); *A61L 15/26* (2013.01);
(Continued)

(58) Field of Classification Search
CPC ............... A61F 13/51113; A61F 2013/51066; A61F 2013/51073; A61F 2013/51117; A61F 2013/8455; A61F 2013/8461; A61L 15/48; A61L 15/50
USPC .......................... 604/364, 367; 424/401, 443
See application file for complete search history.

(56) References Cited

U.S. PATENT DOCUMENTS

| | | | |
|---|---|---|---|
| 5,591,148 A | 1/1997 | McFall et al. | |
| 5,614,178 A | * 3/1997 | Bloom et al. | 424/60 |

(Continued)

FOREIGN PATENT DOCUMENTS

| | | |
|---|---|---|
| GB | 1359970 | 7/1974 |
| WO | WO 03/022235 | 3/2003 |

OTHER PUBLICATIONS

Costa, C.K. et al., "A Dry Skin Study: Emulsion for His Treatment and Search of Sensorial Pleasantness for a Continuous Use," Visao Academica, Curitiba, v. 5, n. 2, pp. 69-78, Jul.-Dec. 2004, ISSN: 1518-5192 (English Abstract) (Translation Abstract Only).

*Primary Examiner* — Lynne Anderson
(74) *Attorney, Agent, or Firm* — Andres E. Velarde; Amanda T. Barry

(57) ABSTRACT

An absorbent article, such as a catamenial device, comprises a liquid pervious topsheet, the topsheet having an inner surface oriented toward the interior of the absorbent article and an outer surface oriented toward the skin of the wearer when the absorbent article is being worn. The absorbent article includes a backsheet joined to the topsheet, the backsheet having an inner surface oriented toward the interior of the absorbent article and an outer surface oriented toward the garment of the wearer when the absorbent article is being worn. The absorbent article includes an absorbent core disposed between the topsheet and the backsheet, the absorbent core having an inner surface oriented toward the skin of the wearer when the absorbent article is being worn and an outer surface oriented toward the garment of the wearer when the absorbent article is being worn. The absorbent article includes a lotion composition applied to at least a portion of the inner surface of the topsheet, the inner surface of the backsheet, and/or a substrate or surface thereof disposed between the inner surface of the topsheet and the inner surface of the backsheet, wherein the lotion composition comprises a polypropylene glycol material.

3 Claims, 3 Drawing Sheets

(52) U.S. Cl.
CPC ..... *A61L 15/34* (2013.01); *A61F 2013/51073* (2013.01); *A61F 2013/8461* (2013.01); *A61L 15/48* (2013.01); *A61L 15/50* (2013.01)

(56) References Cited

U.S. PATENT DOCUMENTS

| | | | |
|---|---|---|---|
| 5,968,025 A * | 10/1999 | Roe et al. | 604/364 |
| 5,998,032 A | 12/1999 | Hansen et al. | |
| 6,149,934 A | 11/2000 | Krzysik et al. | |
| 6,296,862 B1 | 10/2001 | Paul et al. | |
| 6,340,411 B1 | 1/2002 | Hansen et al. | |
| 6,551,604 B1 * | 4/2003 | Beck et al. | 424/401 |
| 6,888,044 B2 | 5/2005 | Fell et al. | |
| 2001/0009991 A1 | 7/2001 | Hisanaka | |
| 2003/0082219 A1 * | 5/2003 | Warren et al. | 424/401 |
| 2004/0102750 A1 | 5/2004 | Jameson | |
| 2005/0010183 A1 | 1/2005 | Miller et al. | |
| 2007/0087041 A1 * | 4/2007 | Luu et al. | 424/443 |

\* cited by examiner

ABSORBENT ARTICLE WITH LOTION COMPRISING A POLYPROPYLENE GLYCOL MATERIAL

CROSS REFERENCE TO RELATED APPLICATION

This application claims the benefit of U.S. Provisional Application Ser. No. 60/901,793 filed Feb. 16, 2007.

FIELD OF INVENTION

This application relates to absorbent articles, including catamenial devices such as tampons and sanitary napkins for the absorption of menses. More particularly, the present invention relates to catamenial devices comprising a lotion composition comprising a polypropylene glycol material, the lotion composition being applied to a surface thereof.

BACKGROUND OF THE INVENTION

Disposable absorbent articles, such as diapers, training pants, and catamenial devices having lotioned topsheets are known. Lotions of various types are known to provide various skin benefits, such as prevention or treatment of diaper rash. These lotions can be applied to the topsheet of absorbent articles, for example, and can be transferred to the skin of the wearer during use.

Unlike many types of disposable absorbent articles, catamenial devices such as pads and pantiliners are specifically designed to acquire menstrual fluid. Menstrual fluid differs from other exudates, such as urine, in many important properties, such as viscosity. Therefore, catamenial devices should differ in their structural components from such devices as baby diapers to be optimized for the maximum absorption of menstrual fluid.

Treatments to the bodyside surface of the topsheet of diaper absorbent products have been proposed to primarily provide skin health benefits and secondarily to allow fluid such as urine to be absorbed into the product. Nonetheless these treatments are known to impede the acquisition of fluid and 'schemes' have been designed to place these treatments on regions of the bodyside surface of the topsheet to minimize their effect on fluid acquisition. Treatments of the bodyside surface of the topsheet of feminine hygiene products have also been proposed to provide skin health benefits and similarly the treatment deployment is generally performed to minimize the hindrance of menstrual fluid acquisition. Nonetheless the use of these topsheet treatments can provoke negative product failure signals to the user of feminine hygiene products including the appearance of a dirty or soiled topsheets or negative odor sensorial signals.

It would be beneficial to have a treatment for feminine hygiene articles that can enable migration of fluid into the product away from the center towards the edges to improve fluid acquisition and capacity.

Additionally, it would be beneficial to have a treatment for feminine hygiene articles that enables migration of fluid, such as menstrual fluid, in a controlled fashion.

Further, it would be beneficial to have a treatment for feminine hygiene articles that facilitates fluid, such as menstrual fluid, being moved so as to enhance perceived cleanliness.

SUMMARY OF THE INVENTION

An absorbent article, such as a catamenial device, comprises a liquid pervious topsheet, the topsheet having an inner surface oriented toward the interior of the absorbent article and an outer surface oriented toward the skin of the wearer when the absorbent article is being worn. The absorbent article includes a backsheet joined to the topsheet, the backsheet having an inner surface oriented toward the interior of the absorbent article and an outer surface oriented toward the garment of the wearer when the absorbent article is being worn. The absorbent article includes an absorbent core disposed between the topsheet and the backsheet, the absorbent core having an inner surface oriented toward the skin of the wearer when the absorbent article is being worn and an outer surface oriented toward the garment of the wearer when the absorbent article is being worn. The absorbent article comprises a lotion composition applied to at least a portion of either the inner surface of the topsheet, the inner surface of the backsheet, and/or any substrate (or surface thereof) disposed between the inner surface of the topsheet and the inner surface of the backsheet (such as the absorbent core), the lotion composition comprising a polypropylene glycol material. If the polypropylene material is applied to a substrate, such as the absorbent core, which comprises an absorbent gelling material, the polypropylene glycol material is not utilized as a binder for the absorbent gelling material. In one embodiment, the lotion composition consists essentially of a polypropylene glycol material. The lotion composition comprising the polypropylene glycol material helps to more evenly distribute the absorbed bodily fluid, such as menses, across and throughout the various components of the absorbent article.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The present invention is directed to absorbent articles, particularly disposable absorbent articles, having thereon a lotion treatment composition, the treatment composition comprising a polypropylene glycol ("PPG") material. Disposable absorbent articles can be baby diapers or feminine hygiene articles, including incontinence devices and catamenial products such as tampons, sanitary napkins, pantiliners, interlabial products, and the like. The invention is disclosed below with respect to one embodiment of a catamenial device, such as a sanitary napkin or pantiliner.

Figure 1:
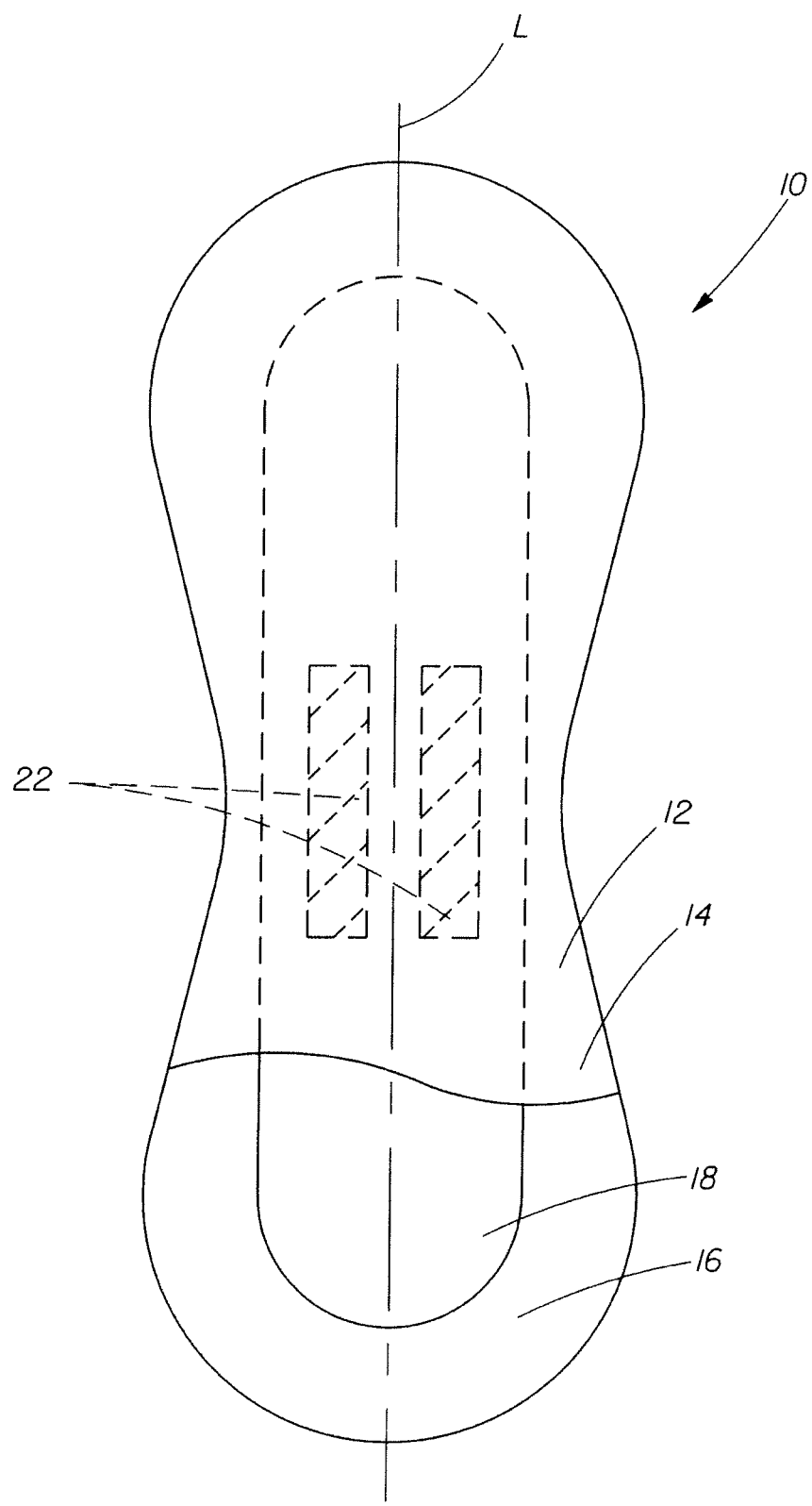
FIG. 1 is a top view of a representative catamenial device having a topsheet, backsheet, and an absorbent core.
Figure 2:
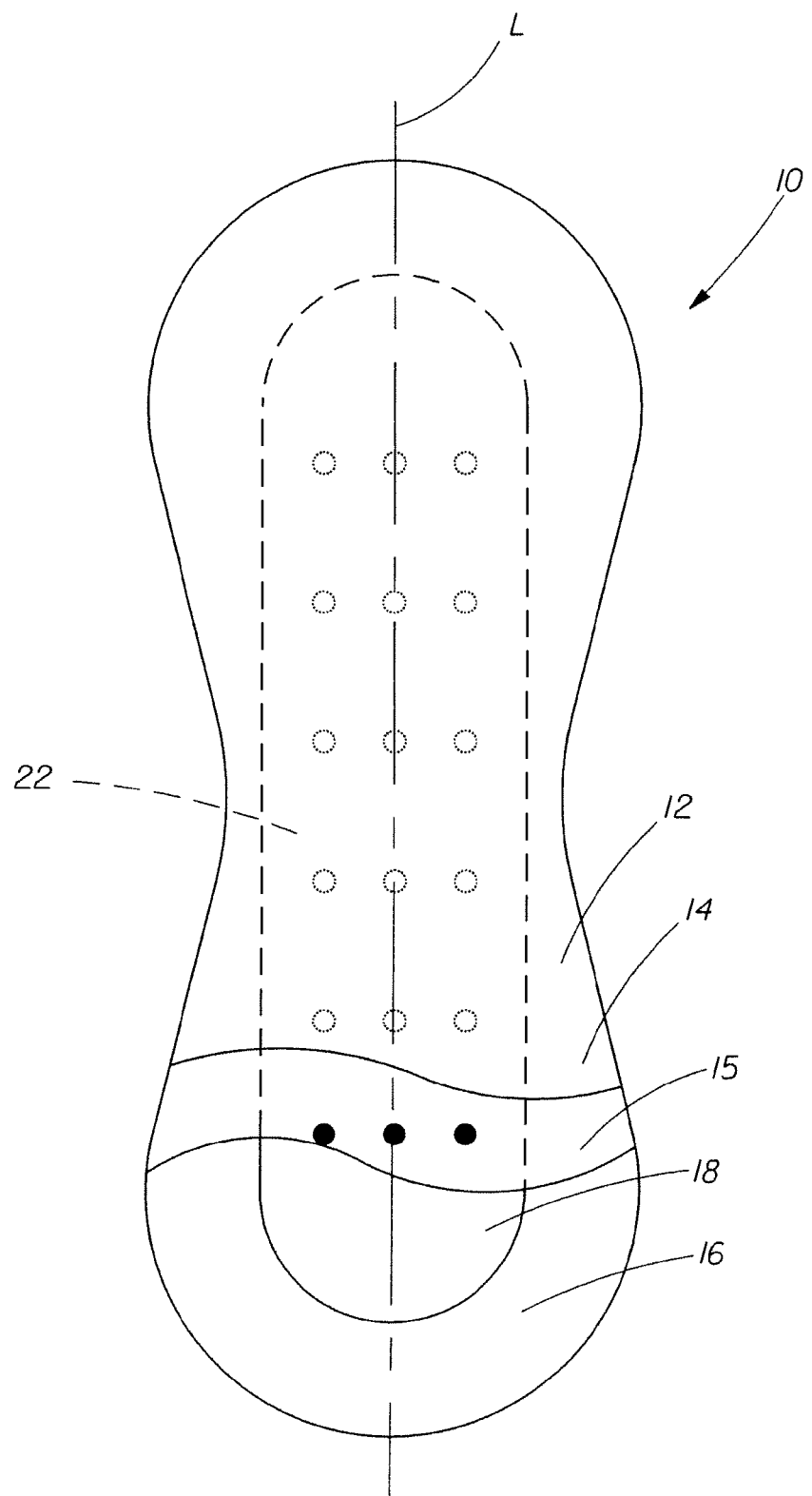
FIG. 2 is a top view of another representative catamenial device having a topsheet, a secondary topsheet, a backsheet, and an absorbent core.
Figure 3:
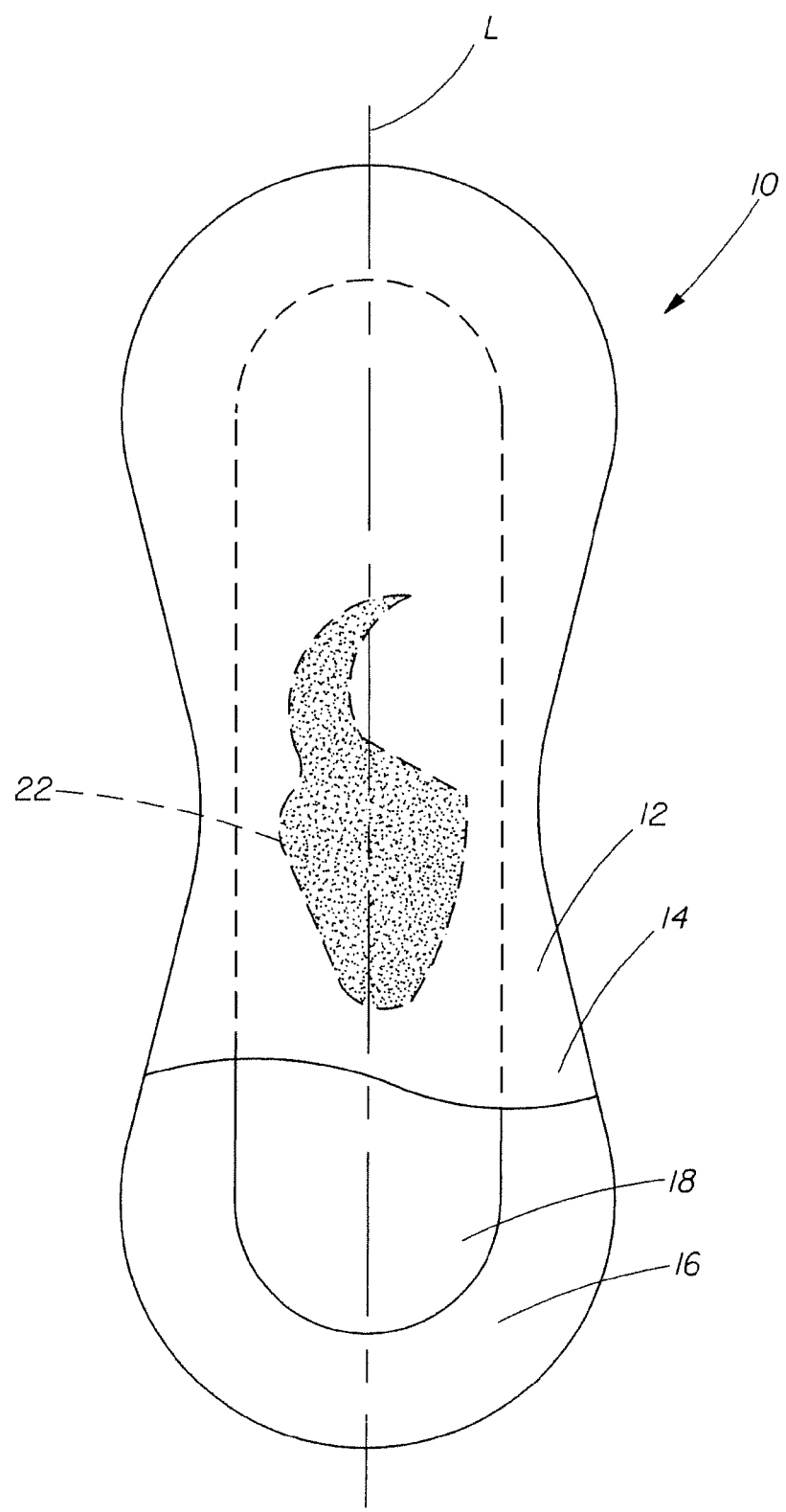
FIG. 3 is a top view of another representative catamenial device having a topsheet, a backsheet, and an absorbent core.

FIGS. 1, 2, and 3 show a catamenial device 10, that can be a sanitary napkin or pantiliner, having a body-contacting surface 12 comprising the outer surface of a topsheet 14, a liquid impervious backsheet 16 joined to the topsheet 14, an absorbent core 18. The catamenial device shown in FIG. 2 further comprises a secondary topsheet 15 disposed between the topsheet 14 and absorbent core 18. The sanitary napkin 10 has a longitudinal axis L and may also be provided with additional features commonly found in napkins, including "wings" or "flaps" (not shown) as is known in the art, and, and/or a secondary topsheet, and/or a fluid acquisition layer, and/or other layers designed to promote fluid transport to the absorbent core 18. Likewise, the topsheet of the sanitary napkin can have various optional characteristics, as is known in the art. For example, the topsheet 14 can have channels embossed therein to direct fluid flow, and can have apertures there through to aid in fluid acquisition, and can have printed signals visible on or through, the visible signals being printed on the topsheet or underlying layers, and visible for functional and aesthetic properties.

The catamenial devices 10 of FIGS. 1, 2, and 3 each have a lotion composition 22 applied thereto. The catamenial device 10 of FIG. 1 has a lotion composition 22 applied in parallel stripes to the inner surface of the backsheet 16. The catamenial device 10 of FIG. 2 has a lotion composition 22 applied in a pattern of dots to the outer surface of the secondary topsheet 15. The catamenial device 10 of FIG. 3 has a lotion composition 22 applied in a non-uniform pattern to the outer surface of the absorbent core 18.

The absorbent article may comprise any known or otherwise effective topsheet, such as one which is compliant, soft feeling, and non-irritating to the wearer's body. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the lotion composition onto an external or internal portion of a wearer's body. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof, as is well known in the art of making catamenial products such as sanitary napkins, pantiliners, incontinence pads, and the like.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The catamenial device of the present invention also comprises a backsheet. The backsheet can be any known or otherwise effective backsheet material, provided that the backsheet prevents external leakage of exudates absorbed and contained in the catamenial device. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making catamenial products such as sanitary napkins, pantiliners, incontinence pads, and the like.

The catamenial device also comprises an absorbent core. The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements. Nonlimiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making catamenial products such as sanitary napkins, pantiliners, incontinence pads, and the like.

The catamenial device of the present invention comprises a lotion composition 22, wherein the lotion composition comprises a PPG material. The PPG lotion composition 22 can be applied in any known manner, in any known pattern, and to any known portion of the catamenial product, as is well known in the art of lotioned catamenial products. For example, the lotion 22 can be applied in a pattern of generally parallel stripes or bands, as depicted in FIG. 1. The lotion treatment composition can be a lotion coating on any part of the device, and on either side of any components, such as outer surfaces, or inner surfaces. Outer surfaces can include surfaces such as the body-facing side of a sanitary napkin topsheet, or the vaginal wall facing surface of a tampon overwrap. Inner surfaces can include surfaces facing the interior of the device.

If disposed on the topsheet or the backsheet, the lotion composition is preferably disposed on the inner surface of the topsheet or backsheet. Traditionally, lotion compositions have been applied to the body facing surface (i.e. outer surface) of topsheets. With respect to applying the lotion composition to the inner surface, as opposed to the body facing surface, of the topsheet, it is believed that the PPG lotion composition helps to reduce adherence of bodily fluid, such as menses, to the fibers of a substrate, thereby facilitating more rapid distribution of the bodily fluid throughout the absorbent article. This allows more efficient utilization of the absorbent capacity of the absorbent article.

The lotion composition can be applied alternatively, or additionally, to any substrate (or surface thereof) disposed between the inner surface of the topsheet and the inner surface of the backsheet. As such, the lotion composition can be disposed on either the inner or outer surface of, and in any pattern on or within, the absorbent core. The lotion composition can be on either the inner or outer surface of, and in any pattern on, other components, such as secondary topsheets, secondary absorbent core materials, distribution layers, and wings. For tampons, the lotion composition can be disposed on the pledget either before or after compression, on the overwrap, the skirt portion, the withdrawal string, and/or any applicator devices. If the catamenial device comprises an absorbent gelling material (such as sometimes found in an absorbent core), the PPG material is not utilized as a binder for the absorbent gelling material. Absorbent gelling materials typically include superabsorbent polymers such as hydrogel-forming polymeric gelling agents.

For catamenial devices the amount of lotion add on level can be variable, and can be tailored for specific needs. For example, while not being bound by theory, it is believed that lotion can be added on at levels of about 0.01 grams per square meter ("gsm"), about 0.05 gsm, about 0.1 gsm, about 0.5, about 1 gsm, about 2 gsm, about 3 gsm, about 4 gsm, about 5 gsm, about 10 gsm, about 25 gsm, about 50 gsm, or about 100 gsm. The lotion can be applied within a range defined by any of the levels recited above (e.g. from about 0.01 gsm to about 100 gsm). These levels refer to the area of the surface actually covered by lotion.

The catamenial device and lotion composition device include components, structure, patterns, formulations, and variations as described in US 2005/0129651 A1, US 2004/0170589 A1, and US 2005/0208113 A1.

The lotion composition 22 of the present invention offers significant advantages over known lotions, including non-PPG derived surfactants and other surface modifying agents. The advantage is particularly important for catamenial articles for absorbing menses. Without being bound by theory, it is believed that the superior fluid handling properties of the PPG materials herein is due to the way the PPG materials act on the solid components of menses as opposed to surface energy treatments which act on the water component of menses. Known surface energy treatments are less effective due to the presence of polar and dispersive components in menses, which complicates the effectiveness of surface energy treatments. Because the PPG materials herein are typically not readily soluble in menses, it can effectively coat surfaces without dissolving in menses, rendering the menses less prone to fouling surfaces of the disposable absorbent article. Less fouling results in better and faster fluid movement, and less visible stain patterns on used products.

The PPG materials herein can be applied as one component in a lotion composition, or can be applied neat (i.e. the lotion composition consists of PPG material). PPG materials can be applied at varying add-on levels, depending on the fluid handling properties desired. PPG materials can be added to any portion of a disposable absorbent product, such as the topsheet, backsheet, absorbent core, wings, secondary topsheet, or withdrawal cord (for tampons), and can be added on in any pattern, such as full coat, stripes or bands (in the MD or CD direction), droplets, spiral patterns, and the like. The lotion composition comprising the PPG material can also be disposed near channels or embossed areas when present in the absorbent article.

In one embodiment, the topsheet 14 can be hydrophilic or rendered to be hydrophilic, and the lotion can be also hydrophilic. The levels of hydrophilicity or hydrophobicity can be determined by standard techniques, such as measuring angles that a drop of water make on a surface of material at equilibrium. In general, for the purposes of this invention, a material is considered hydrophilic if a drop of water exhibits an angle of about 60 degrees or less. Fibers are considered to be hydrophilic if film sheets formed from the polymers of the fibers would exhibit contact angles with water less than 60 degrees, more less than 75 degrees, and less than about 90 degrees. Contact angles as a measure of hydrophilicity are well known in the art, and methods for measuring contact angles are equally well known. As is well known, contact angles greater than about 90 degrees are considered hydrophobic, and contact angles less than 90 degrees are considered hydrophilic.

The lotion composition of the present invention comprises a PPG material. The PPG materials suitable herein include PPG homopolymer materials, PPG copolymer materials, and PPG surfactant materials, as well as mixtures thereof. The lotion composition can further comprise other optional ingredients. In one embodiment, the lotion composition consists essentially of, or consists of, a PPG material, preferably polypropylene glycol.

Suitable PPG homopolymer materials include those corresponding to the following formula:

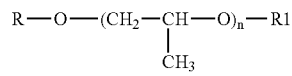

wherein R is hydrogen, methyl, ethyl, propyl, isopropyl, butyl, isobutyl, benzyl, aceto carbonyl, propio carbonyl, butyro carbonyl, isobutyro carbonyl, benzo carbonyl, fumaro carbonyl, aminobenzo carbonyl, carboxymethylene, aminopropylene, alkylated glucose, alkylated sucrose, alkylated cellulose, alkylated starch or phosphate; and wherein R is preferably hydrogen or methyl;

wherein R1 is hydrogen, methyl, ethyl, propyl, isopropyl, butyl, isobutyl, benzyl, aceto carbonyl, propio carbonyl, butyro carbonyl, isobutyro carbonyl, benzo carbonyl, fumaro carbonyl, aminobenzo carbonyl, carboxymethylene, aminopropylene, alkylated glucose, alkylated sucrose, alkylated cellulose, alkylated starch or phosphate; and wherein R1 is preferably hydrogen or methyl; and wherein n is from 3 to 160, preferably from 10 to 100, and more preferably from 20 to 80.

Optionally, the PPG homopolymer may include low level of glycerol or butanediol as part of its monomer raw material. If in presence, the preferred ratio of glycerol or butanediol to propylene glycol ranges from 1:1000 to 1:2, most preferably 1:100 to 1:5. The PPG homopolymer can have, but not limited to, the CAS Number 25322-69-4 and 25791-96-2.

Non-limiting examples of suitable PPG homopolymer materials are polypropylene glycol 4000 such as Pluriol P-4000 (BASF), Alkapol PPG-4000 (Alkaril Chemical) and Niax Polyol PPG 4025 (Union Carbide); polypropylene glycol 3500; polypropylene glycol 3000 such as Niax PPG 3025 (Union Carbide); polypropylene glycol 2000 such as Alkanol PPG-2000 (Alkaril Chemical) and Pluriol P-2000 (BASF), polypropylene glycol 1200 such as Alkapol PPG-1200 (Alkaril Chemical) and Glucam P-20 Humectant (Noveon); polypropylene glycol 1000 such as Niax PPG 1025 (Union Carbide); polypropylene glycol 600 such as Alkanol PPG-600 (Alkaril Chemical) and Glucam P-10 Humectant (Noveon); polypropylene glycol 400 such as Alkanol PPG-425 (Alkaril Chemical). polypropylene glycol 4000 glycerol ether such as Pluriol T-4000 (BASF); polypropylene glycol 2000 glycerol ether, polypropylene glycol 2000 butanediol ether, polypropylene glycol 1500 glycerol ether such as Pluriol T-1500 (BASF), polypolypropylene glycol 4000 with monomethyl ether, polypropylene glycol 2000 with dimethyl ether, polypropylene glycol 4000 with monobutyl ether, polypropylene glycol 2000 with monobuytyl ether, polypropylene glycol 1200 with dibutyl ether, polypropylene glycol 4000 with bis(2-aminopropyl ether), PPG-10 methyl glucose ether and PPG-20 methyl glucose either Suitable PPG copolymer materials include those in which the polyprolyene glycol segments are present as an internal block component and/or as a terminal component, of the copolymer structure. The following formulae illustrate the internal block components and terminal block components:

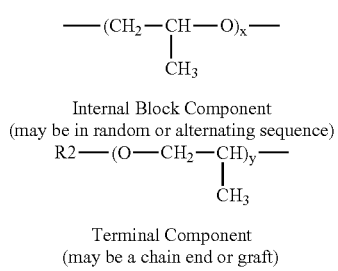

Internal Block Component
(may be in random or alternating sequence)

Terminal Component
(may be a chain end or graft)

wherein x is from 2 to 120, preferably from 2 to 80, and more preferably from 3 to 60; y is from 2 to 100, preferably from 2 to 50, and more preferably from 3 to 30; and R2 is hydrogen, methyl, ethyl, isopropyl or isobutyl.

The polymers suitable to form propoxylated copolymer with PPG for the present lotion compositions include polydimethyl siloxane, polyethylimine, polyacrylic acid, poly(ethylene-co-acrylic acid), polymethacrylic acid, poly(ethylene-co-methacrylic acid), poly(vinyl acetate), polyvinylpyrrolidone, poly(ethylene-co-vinyl acetate), poly(butanediol), poly(neopentyl glycol), poly(ethylene adipate), poly(butylene adipate), poly(ethylene glutamate), poly(butylene glutamate), poly(ethylene sebacate), poly(butylene sebacate), poly(ethylene succinate), poly(butylene succinate), poly(ethylene terephthalate), poly(butylene terephthalate), polycaprolactone, and polyglycerol.

Non-limiting examples of suitable PPG copolymer materials include PPG-12 dimethicone such as Sisoft 910 (Momentive); bis-PPG-15 dimethicon/IDI copolymer such as Polyderm-PPI-SI-WI (Alzo); PPG/polycaprolactone block copolymer; PPG/polybutanediol/PEG random copolymer; PPG/polybutanediol/PEG tribolck copolymer; polyimine/PPG copolymer and polyacrylic acid-g-PPG copolymer.

Another suitable PPG material includes PPG surfactant materials. The following formula represents suitable PPG surfactant materials wherein the PPG segments constitute a part of the head functional group:

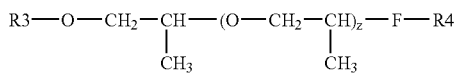

wherein R3 is hydrogen, alkyl, alkyl carbonyl, alkylenelamine, alkylenelamide, alkylene phosphate, alkylene carboxylic acid, alkylene sulfonate salt and alkylene quat with the maximum number of carbon element less than or equal to 6; R4 is octyl, nonyl, decyl, iosdecyl, lauryl, myristyl, cetyl, isohexadecyl, oleyl, stearyl, isostearyl, tallowoyl, linoleyl, jojoba, lanolin, behenyl, dinonylphenyl, dodecyl phenyl, or soya; z is from 1 to 100, preferably from 2 to 30, and more preferably from 3 to 25; and F is a functional group selected from the group consisting of ether groups (including oxy, glyceryl, glucose, sorbitan, sucrose, monoethanolamine or diethanolamine), ester groups (including ester, glyceryl ester, glucose ester, sorbitan ester or sucrose ester), amine groups, amide groups, and phosphate ester groups.

The following formula represents suitable PPG surfactant materials wherein the PPG segments constitute an internal block group:

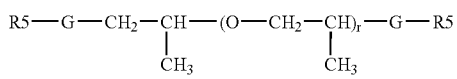

wherein R5 is hexyl, 2-ethylhexyl, octyl, nonyl, decyl, isodecyl, lauryl, cocoyl, myristyl, cetyl, isohexadecyl, oleyl, stearyl, isostearyl, tallow, linoleyl, octyl phenyl, or nonyl phenyl; r is from 1 to 120, preferably from 4 to 50, and more preferably from 6 to 30; and G is ether, ester, amine, or amide linkage.

Non-limiting examples of suitable PPG surfactant materials include PPG-30 cetyl ether such as Hetoxol C30P (Global Seven); PPG-20 methyl glucose ether distearate such as Glucam P-20 Distearate Emollient (Noveon), PPG-20 methyl glucose ether acetate, PPG-20 sorbitan tristearate, PPG-20 methyl glucose ether distearate, PPG-20 distearate, PPG-15 stearyl ether such as Alamol-E (Croda-Uniqema) and Procetyl 15 (Croda), PPG-15 stearyl ether benzoate, PPG-15 isohexadecyl ether, PPG-15 stearate, PPG-15 dicocoate, PPG-12 dilaurate, PPG-11 stearyl ether such as Varonic APS (Evonik); PPG-10 cetyl ether such as Procetyl 10 (Croda); PPG-10 glyceryl stearate, PPG-10 sorbitan monosteate, PPG-10 hydrogenated castor oil, PPG-10 cetyl phosphate, PPG-10 tallow amine, PPG-10 oleamide, PPG-10 cetyl ether phosphate, PPG-10 dinonylphenolate, PPG-9 laurate, PPG-8 dioctate, PPG-8 diethylhexylate, PPG-7 lauryl ether, PPG-5 lanolin wax ether, PPG-5 sucrose cocoate, PPG-5 lanolin wax, PPG-4 jojoba alcohol ether, PPG-4 lauryl ether, PPG-3 myristyl ether such as Promyristyl PM-3 (Croda), PPG-3 myristyl ether propionate such as Crodamol PMP (Croda), PPG-3 benzyl ether myristate such as Crodamol STS (Croda), PPG-3 hydrogenated castor oil such as Hetester HCP (Alzo), PPG-3-hdyroxyethyl soyamide, PPG-2 Cocamide, PPG-2 lanolin alcohol ether and PPG-1 coconut fatty acid isopropanolamide such as Amizett IPC (Kawaken Fine Chemicals).

In addition to PPG materials, the lotion compositions of the present invention can optionally further comprise a select combination of body treatment agents such as hexamidine, zinc oxide, and niacinamide which are highly effective in the prevention and treatment of erythema, malodor, and bacterial skin disorders, especially when these lotion compositions are administered to the body from application on absorbent articles.

The lotion compositions of the present invention can optionally further comprise a carrier for the PPG material and/or optional body treatment agents. The carrier can be included in the compositions as an individual carrier or a combination of carrier ingredients, provided that the total carrier concentration is sufficient to provide transfer and/or migration of the PPG material and/or optional body treatment agents onto the body and to promote fluid acquisition into the absorbent article. The carrier can be a liquid, solid, or semisolid carrier material, or a combination of these materials, provided that the resultant carrier forms a homogenous mixture or solution at selected processing temperatures for the resultant carrier system and at processing temperatures for combining the carrier with the skin treatment agents in formulating the lotion compositions herein. Processing temperatures for the carrier system may range from about 60° C. to about 90° C., more typically from about 70° C. to about 85° C., even more typically from about 70° C. to about 80° C.

The lotion compositions of the present invention can comprise the carrier at a total carrier concentration ranging from about 60% to about 99.9%, preferably from about 70% to about 98%, more preferably from about 80% to about 97% by weight of the lotion composition. Suitable carrier compounds include petroleum-based hydrocarbons having from about 4 to about 32 carbon atoms, fatty alcohols having from about 12 to about 24 carbon atoms, polysiloxane compounds, fatty acid esters, alkyl ethoxylates, lower alcohols having from about 1 to about 6 carbon atoms, low molecular weight glycols and polyols, fatty alcohol ethers having from about 12 to about 28 carbon atoms in their fatty chain, lanolin and its derivatives, glyceride and its derivatives including acetoglycerides and ethoxylated glycerides of C12-C28 fatty acids, and mixtures thereof. Alternatively or in combination with, the carrier may also be composed of polysiloxane compounds non-limiting examples include dimethicones (1-100,000,000 centistoke), cyclomethicones, alkylated silicones (hair conditioning agents), silicone gums, silicone gels, silicone waxes, copolymers of silicone (vinyl dimethicone polymers, phenyl vinyl dimethicone polymers, alkylated silicone polymers, polyethylene oxide/silicone copolymers, polyethylene oxide/alkyl silicone copolymers), and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as Protopet® 1S which is available from the Witco Corporation located in Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol carriers for use in the lotion compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol is Stenol 1822 and behenyl alcohol is Lanette 22, both of which are available from the Cognis Corporation located in Cincinnati, Ohio.

Nonlimiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Nonlimiting examples of suitable alkyl ethoxylates include $C_{12}$-$C_{22}$ fatty alcohol ethoxylates having an average degree of ethoxylation of from about 2 to about 30. Nonlimiting examples of suitable lower alcohols having from about 1 to about 6 carbon atoms include ethanol, isopropanol, butanediol, 1,2,4-butanetriol, 1,2 hexanediol, ether propanol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol and mixtures thereof. A more detailed description of carrier ingredients including suitable hydrocarbons, polysiloxane compounds, and fatty alcohol ethoxylates can be found in U.S. Pat. No. 5,643,588, issued Jul. 1, 1997 to Roe et al. entitled "Diaper Having A Lotioned Topsheet".

In preparing lotioned catamenial device according to the present invention, the lotion composition is applied to at least a portion of either the inner surface of the topsheet, the inner surface of the backsheet, or any substrate (or surface thereof) disposed between the inner surface of the topsheet and the inner surface of the backsheet (such as the absorbent core). Any of a variety of application methods that distribute lubricious materials having a molten or liquid consistency can be used. Suitable methods include but are not limited to spraying, printing (e.g., flexographic printing), coating (e.g., gravure coating), extrusion, dipping, or combinations of these application techniques, e.g. spraying the lotion composition on a rotating surface, such as a calender roll, that then transfers the composition to the outer surface of the sanitary napkin topsheet. Additionally, the manner of applying the lotion composition to a portion of a catamenial device can be such that the substrate or component does not become saturated with the lotion composition.

The minimum level of the lotion composition to be applied to a component of the catamenial device is an amount effective for reducing the adherence of menses to that component.

The lotion composition can also be applied nonuniformly to a component or layer of the catamnial device. By "non-uniform" is meant that the amount, pattern of distribution, etc. of the lotion composition can vary. For example, a non-uniform pattern of lotion composition 22 is shown in FIG. 3.

The lotion composition can be applied to the catamenial device at any point during assembly. For example, the lotion composition can also be applied to a portion of the device before it is combined with the other raw materials to form a finished catamenial device.

Lotion compositions of the present invention can be applied by printing methods, or continuous spray or extrusion as is known in the art, or as is disclosed in U.S. Pat. No. 5,968,025.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a liquid pervious topsheet, said topsheet having an inner surface oriented toward the interior of said absorbent article and an outer surface oriented toward the skin of the wearer when said absorbent article is being worn,
a backsheet joined to said topsheet, said backsheet having an inner surface oriented toward the interior of said absorbent article and an outer surface oriented toward the garment of the wearer when said absorbent article is being worn;
an absorbent core disposed between said topsheet and said backsheet, said absorbent core having an inner surface oriented toward the skin of the wearer when said absorbent article is being worn and an outer surface oriented toward the garment of the wearer when said absorbent article is being worn;
and a lotion composition applied to at least a portion of said inner surface of said topsheet, said inner surface of said backsheet, and/or a substrate or surface thereof disposed between said inner surface of said topsheet and said inner surface of said backsheet, said lotion composition consisting essentially of a polypropylene glycol material;
wherein said polypropylene glycol material is a polypropylene glycol surfactant material selected from the group consisting of: PPG-30 cetyl ether, PPG-20 methyl glucose ether distearate, PPG-20 methyl glucose ether acetate, PPG-20 sorbitan tristearate, PPG-20 methyl glucose ether distearate, PPG-20 distearate, PPG-15 stearyl ether, PPG-15 stearyl ether benzoate, PPG-15 isohexadecyl ether, PPG-15 stearate, PPG-15 dicocoate, PPG-12 dilaurate, PPG-11 stearyl ether, PPG-10 cetyl ether, PPG-10 glyceryl stearate, PPG-10 sorbitan monosteate, PPG-10 hydrogenated castor oil, PPG-10 cetyl phosphate, PPG-10 tallow amine, PPG-10 oleamide, PPG-10 cetyl ether phosphate, PPG-10 dinonylphenolate, PPG-9 laurate, PPG-8 dioctate, PPG-8 diethylhexylate, PPG-7 lauryl ether, PPG-5 lanolin wax ether, PPG-5 sucrose cocoate, PPG-5 lanolin wax, PPG-4 jojoba alcohol ether, PPG-4 lauryl ether, PPG-3 myristyl ether, PPG-3 myristyl ether, PPG-3 benzyl ether myristate, PPG-3 hydrogenated castor oil, PPG-3-hdyroxyethyl soyamide, PPG-2 Cocamide, PPG-2 lanolin alcohol ether, and PPG-1 coconut fatty acid isopropanolamide, and combinations thereof.

2. The absorbent article of claim 1, wherein said absorbent article is a catamenial device selected from the group consisting of a sanitary napkin and a pantiliner.

3. The absorbent article of claim 1, wherein said topsheet is selected from the group consisting of a nonwoven material and a formed film material.

* * * * *